United States Patent
Lee et al.

(10) Patent No.: US 11,320,425 B2
(45) Date of Patent: May 3, 2022

(54) ENHANCED INFRARED RAY ABSORBING/EMITTING NANOPARTICLES AND ON-SITE DIAGNOSIS KIT USING SAME

(71) Applicant: KOREA INSTITUTE OF SCIENCE AND TECHNOLOGY, Seoul (KR)

(72) Inventors: Joon Seok Lee, Seoul (KR); Seok Lee, Seoul (KR); Man Ho Choi, Seoul (KR); Hee Soo Pyo, Seoul (KR); Seung Ki Kim, Seoul (KR); Jae Young Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 101 days.

(21) Appl. No.: 16/341,852

(22) PCT Filed: Mar. 6, 2018

(86) PCT No.: PCT/KR2018/002616
§ 371 (c)(1),
(2) Date: Apr. 12, 2019

(87) PCT Pub. No.: WO2019/009495
PCT Pub. Date: Jan. 10, 2019

(65) Prior Publication Data
US 2019/0324027 A1 Oct. 24, 2019

(30) Foreign Application Priority Data

Jul. 7, 2017 (KR) .................. 10-2017-0086300
Jan. 25, 2018 (KR) .................. 10-2018-0009062

(51) Int. Cl.
*G01N 33/543* (2006.01)
*C09K 11/02* (2006.01)
*C09K 11/77* (2006.01)
*G01N 21/3577* (2014.01)

(52) U.S. Cl.
CPC ........ *G01N 33/54346* (2013.01); *C09K 11/02* (2013.01); *C09K 11/7766* (2013.01); *G01N 21/3577* (2013.01); *G01N 33/54306* (2013.01)

(58) Field of Classification Search
CPC ......... G01N 33/54346; G01N 21/3577; G01N 33/54306; G01N 33/587; G01N 33/558; C09K 11/02; C09K 11/7766; C09K 11/77
See application file for complete search history.

(56) References Cited

FOREIGN PATENT DOCUMENTS

| JP | 2007-046022 A | 2/2007 |
|----|----|----|
| JP | 2009-249507 A | 10/2009 |
| KR | 10-2008-0031996 A | 4/2008 |
| KR | 10-2013-0093301 A | 8/2013 |
| KR | 10-2017-0017266 A | 2/2017 |

OTHER PUBLICATIONS

Li et al. ("Engineering Homogeneous Doping in Single Nanoparticle To Enhance Upconversion Efficiency", Nano Lett., vol. 14, pp. 3634-3639, published May 29, 2014). (Year: 2014).*
Rinkel et al. ("Ostwald-ripening and particle size focussing of sub-10 nm NaYF4 upconversion nanocrystals", Nanoscale, vol. 6, pp. 14523-14530, published Sep. 20, 2014). (Year: 2014).*
Ding et al. ("Facile synthesis of β—NaGdF4:Yb/Er@CaF2 nanoparticles with enhanced upconversion fluorescence and stability via a sequential growth process." CrystEngComm., vol. 17, pp. 5900-5905, published Jul. 6, 2015) (Year: 2015).*
Guanying Chen et al., (α—NaYbF4:Tm3+)/CaF2 Core/Shell Nanoparticles with Efficient Near-Infrared to Near-Infrared Upconversion for High-Contrast Deep Tissue Bioimaging , ACSNANO, Aug. 28, 2012, pp. 8280-8287, vol. 6, No. 9.

* cited by examiner

*Primary Examiner* — Tracy Vivlemore
*Assistant Examiner* — Nam P Nguyen
(74) *Attorney, Agent, or Firm* — Goldilocks Zone IP Law

(57) ABSTRACT

Disclosed is a diagnostic kit for quickly diagnosing a target material with high sensitivity using nanoparticles that absorb infrared light and emit infrared light, in which the nanoparticles are maintained in particle size and have enhanced emission intensity.

11 Claims, 7 Drawing Sheets

ENHANCED INFRARED RAY ABSORBING/EMITTING NANOPARTICLES AND ON-SITE DIAGNOSIS KIT USING SAME

CROSS-REFERENCE TO RELATED APPLICATIONS

This application claims the benefit under 35 U.S.C. section 371, of PCT International Application No.: PCT/KR2018/002616, filed on Mar. 6, 2018, which claims foreign priority to Korean Patent Application No.: KR10-2017-0086300, filed on Jul. 7, 2017, and Korean Patent Application No.: KR10-2018-0009062, filed on Jan. 25, 2018, in the Korean Intellectual Property Office, both of which are hereby incorporated by reference in their entireties.

TECHNICAL FIELD

The present invention relates to a diagnostic kit for quickly diagnosing a target material with high sensitivity using nanoparticles that absorb infrared light and emit infrared light, in which the nanoparticles are maintained in particle size and have enhanced emission intensity.

BACKGROUND ART

An on-site immunoassay diagnostic kit (a lateral flow immunoassay kit (LFA)) is a suitable diagnostic platform for the user to directly detect a target material on site because of the high economic feasibility and convenience thereof.

Although the diagnostic kit is based on an immunoassay technique and may thus be applied to all tests in which an antigen and an antibody are present, the conventional kit is problematic because the color change of the test line has to be visually judged, and also because the sensitivity is lowered due to signal interference depending on the kind of specimen. For example, like a pregnancy diagnostic kit, there is a restriction in that a biomarker such as a HCG hormone should be present at a high concentration in a specimen, or in that the type of specimen is limited.

Commercially available on-site immunoassay diagnostic kits include kits for detecting a target material using color change of gold nanoparticles, a visible light fluorescence signal of quantum dots, as in the following Patent Literature, or chemical signal amplification.

PATENT LITERATURE

Korean Patent No. 10-1053473 (Registration Date: Jul. 27, 2011) "Steroid hormone detection kit and method using quantum dots"

However, the kit using the color change of the gold nanoparticles has low sensitivity, and the detection result thereof is not uniform due to the influence of the specimen. The kit using the visible light fluorescence signal of quantum dots has high sensitivity by virtue of the high emission efficiency of quantum dots compared to the kit using the gold nanoparticles, but is problematic in that ultraviolet light for quantum dot emission generates autofluorescence of the specimen and the kit constituents (plastics, various pads) and the fluorescence of visible light is interfered with by the specimen, and still affects sensitivity. The method using chemical signal amplification is not suitable for an on-site diagnostic kit because large analysis equipment and skilled experts are needed.

DISCLOSURE

Technical Problem

Accordingly, an objective of the present invention is to provide a diagnostic kit for the detection of a target material with high sensitivity, without any influence from a specimen, using nanoparticles that absorb infrared light and emit infrared light, in which the nanoparticles are maintained in particle size and have enhanced emission intensity.

Technical Solution

In order to accomplish the above objective, the present invention is implemented by the following embodiments.

According to an embodiment of the present invention, nanoparticles of the present invention are characterized in that the nanoparticles are doped with a rare earth element and a heterogeneous dopant and absorb infrared light and emit infrared light.

According to another embodiment of the present invention, nanoparticles of the present invention are characterized in that the nanoparticles are doped with a rare earth element and absorb infrared light and emit infrared light, and the nanoparticles are further doped with a heterogeneous dopant to increase the distortion of a crystal structure in the nanoparticles so as to enable sensitive electron transfer.

Also, the nanoparticles of the present invention are characterized in that the emission intensity of the nanoparticles may be controlled by adjusting the kind or concentration of the heterogeneous dopant.

Also, the nanoparticles of the present invention are characterized in that the rare earth element includes at least one selected from the group consisting of Y, Er, Yb, Tm and Nd.

Also, the nanoparticles of the present invention are characterized in that the rare earth element includes 50 mol % of Y, 48 mol % of Yb and 2 mol % of Tm.

Also, the nanoparticles of the present invention are characterized in that the heterogeneous dopant includes at least one selected from the group consisting of Ca, Si, Ni and Ti.

Also, the nanoparticles of the present invention are characterized in that the wavelength of infrared light that is absorbed and the wavelength of infrared light that is emitted are different from each other so that there is no interference between the infrared light that is absorbed and the infrared light that is emitted.

Also, the nanoparticles of the present invention are characterized in that they absorb infrared light having a wavelength of 960 to 980 nm and emit infrared light having a wavelength of 750 to 850 nm.

Also, the nanoparticles of the present invention are characterized in that they include a core layer comprising particles doped with a rare earth element, and a shell layer surrounding the core layer to thus reduce surface defects so as to improve surface uniformity and further doped with a heterogeneous dopant.

Also, the nanoparticles of the present invention are characterized in that they further include a coating layer formed on the outer surface of the shell layer through coating with a monomer or a polymer to thus increase the dispersibility of the nanoparticles in a fluid and facilitate immobilization of a capture agent.

Also, the nanoparticles of the present invention are characterized in that the core layer is provided in the form of nanoparticles by mixing 1-octadecene, oleic acid and a rare earth element to afford a homogenous solution, which is then mixed with methanol containing sodium hydroxide and ammonium fluoride, stirred, and allowed to react at a predetermined temperature for a predetermined period of time, and the shell layer is formed at a predetermined thickness on the core layer by mixing 1-octadecene, oleic acid, a rare earth element and a heterogeneous dopant to afford a homogenous solution, which is then mixed with methanol containing sodium hydroxide and ammonium fluoride and with the core layer, stirred, and allowed to react at a predetermined temperature for a predetermined period of time.

According to still another embodiment of the present invention, a capture-agent/nanoparticle conjugate of the present invention is characterized in that it includes nanoparticles, which absorb infrared light and emit infrared light, and a capture agent binding to the nanoparticles so as to specifically bind to a target material, in which the nanoparticles are the nanoparticles of claim 10, and the capture agent binds to the coating layer.

Also, the capture-agent/nanoparticle conjugate of the present invention is characterized in that the capture agent includes an antibody or an aptamer.

According to yet another embodiment of the present invention, a diagnostic kit of the present invention, which reacts with a target material by unidirectionally moving a specimen containing the target material, is characterized in that it includes a capture-agent/nanoparticle conjugate, specifically binding to the target material and absorbing infrared light and emitting infrared light, and a second capture agent specifically binding to the target material, in which the target material bound to the capture-agent/nanoparticle conjugate binds to the second capture agent during movement of the specimen, and the capture-agent/nanoparticle conjugate is the capture-agent/nanoparticle conjugate of claim 12.

Also, the diagnostic kit of the present invention is characterized in that it further includes a third capture agent specifically binding to the capture agent.

Also, the diagnostic kit of the present invention is characterized in that the capture-agent/nanoparticle conjugate moves together with the specimen, the second capture agent and the third capture agent are immobilized on the diagnostic kit by a predetermined interval, and when the diagnostic kit is irradiated with infrared light, the capture-agent/nanoparticle conjugate bound to the second capture agent and the capture-agent/nanoparticle conjugate bound to the third capture agent emit infrared light.

Also, the diagnostic kit of the present invention is characterized in that the second capture agent is immobilized on the test line of the diagnostic kit, the third capture agent is immobilized on the control line of the diagnostic kit, and the test line is located in front of the control line.

According to still yet another embodiment of the present invention, a diagnostic device of the present invention is characterized in that it includes a diagnostic kit and an infrared light reader configured to accommodate the diagnostic kit and to apply infrared light to the diagnostic kit and measure infrared light emitted from the diagnostic kit to thus provide imaged data to an external terminal, in which the diagnostic kit is the diagnostic kit of claim 16.

Also, the diagnostic device of the present invention is characterized in that the infrared light reader includes a housing, constituting the outer shape of the infrared light reader, and a controller configured to apply infrared light to the diagnostic kit located in the housing and inserted through an insertion groove in the housing and to measure infrared light emitted from the diagnostic kit to thus provide the imaged data to the external terminal.

Also, the diagnostic device of the present invention is characterized in that the controller includes an interface unit for exchanging information with the terminal, a battery for supplying power necessary for the operation of the controller, an irradiation unit for applying infrared light to a membrane of the diagnostic kit located in the housing, an optical unit for photographing infrared light emitted from the membrane after the infrared light is applied to the membrane by the irradiation unit, and an image-processing unit for digitizing and outputting the photographed image output from the optical unit.

Advantageous Effects

According to the embodiments of the present invention, the following effects can be obtained.

In the present invention, a substance to be detected by the user can be quickly diagnosed on site from various specimens such as saliva, blood, stool, beverages, and soil. Further, in the present invention, nanoparticles that absorb infrared light and emit infrared light rather than visible light are used, and thus sample permeation becomes possible due to the long wavelength and a background signal does not occur. Thereby, since there is no interference between light absorption and light emission, the substance to be detected by the user can be detected with high sensitivity. Furthermore, in the present invention, a target material can be detected with higher sensitivity by further enhancing the emission intensity of nanoparticles that absorb infrared light and emit infrared light.

Therefore, the present invention can be applied to pathogens such as *Bacillus anthracis* and botulinum neurotoxin, animal viruses such as foot-and-mouth disease and avian influenza, diseases such as cancer and cardiovascular diseases, or biomarkers for pregnancy diagnosis.

DESCRIPTION OF DRAWINGS

FIG. 13 shows the results of emission spectra of nanoparticles according to an embodiment of the present invention; and FIG. 14 shows camera images of the analytical results of a specimen using the diagnostic kit according to an embodiment of the present invention.

DESCRIPTION OF THE REFERENCE NUMERALS IN THE DRAWINGS

Figure 1:
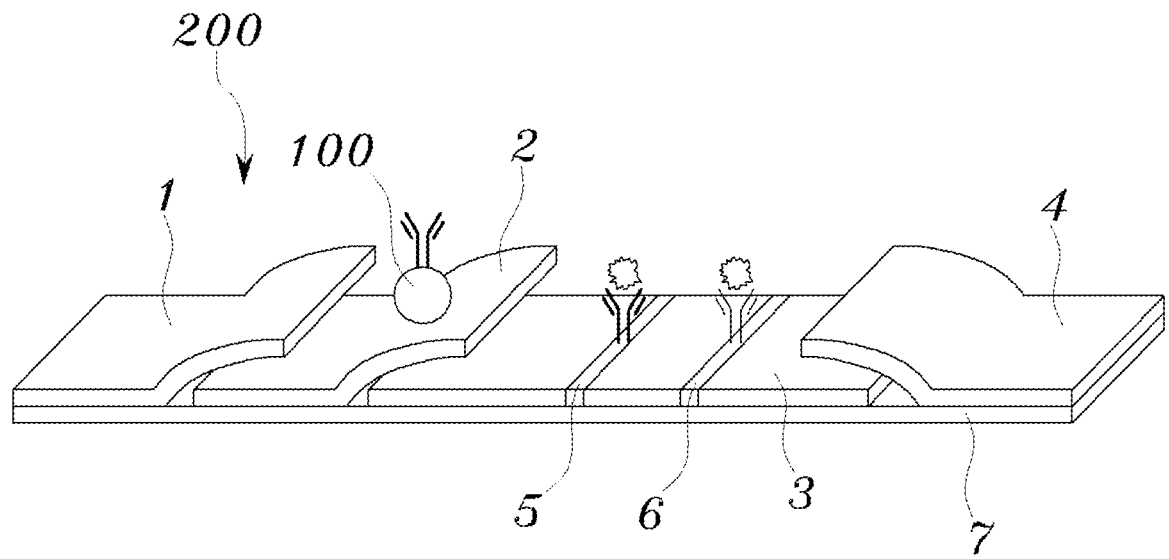
FIG. 1 schematically shows a diagnostic kit according to an embodiment of the present invention.

1: sample pad 2: conjugation pad 3: membrane
4: absorption pad 5: test line 6: control line
7: substrate 100: capture-agent/nanoparticle conjugate
200: diagnostic kit
300: infrared light reader 400: terminal

BEST MODE

Hereinafter, a detailed description will be given of enhanced nanoparticles absorbing and emitting infrared light and an on-site diagnostic kit using the same according to the present invention, with reference to the appended drawings. Unless otherwise defined, all terms used herein have the same meanings as those commonly understood by one of ordinary skill in the art to which the present invention belongs. If the meaning of a term used herein conflicts with the general meaning thereof, the definition used herein shall prevail. In the following description of the present invention, detailed descriptions of known constructions and functions incorporated herein will be omitted when they may make the gist of the present invention unclear. As used herein, when any part "includes" any element, it means that other elements are not precluded but may be further included, unless otherwise mentioned.

According to an embodiment of the present invention, an on-site diagnostic kit using enhanced nanoparticles absorbing and emitting infrared light is described with reference to FIG. 1, and the diagnostic kit 200 is configured to include a sample pad 1, a conjugation pad 2, a membrane 3, an absorption pad 4 and a substrate 7, in which the sample pad 1, the conjugation pad 2, the membrane 3 and the absorption pad 4 are sequentially connected in a direction of movement of the specimen on the substrate 7.

The sample pad 1 is a pad that absorbs a specimen and enables the diffusion flow of a target material to be analyzed. In the present invention, the specimen indicates a substance suspected of containing the target material to be analyzed, and may be referred to as a sample, and the target material refers to a substance to be analyzed for the concentration or presence thereof.

The conjugation pad 2 is a pad configured to include a capture-agent/nanoparticle conjugate 100 and to receive the specimen moved from the sample pad 1 to thus allow the capture-agent/nanoparticle conjugate 100 and the target material contained in the specimen to bind to each other. The capture-agent/nanoparticle conjugate 100 that binds to the target material, which is an analyte in the specimen, may be included in a dry state in the conjugation pad 2. When a liquid specimen is applied to the sample pad 1, the liquid specimen is allowed to wet the dry sample pad 1 therewith, and then moves to the conjugation pad 2, whereby the target material contained in the specimen specifically binds to the capture agent of the capture-agent/nanoparticle conjugate 100.

The capture-agent/nanoparticle conjugate 100 includes nanoparticles doped with a rare earth element and a heterogeneous dopant and absorbing infrared light and emitting infrared light, and a capture agent binding to the nanoparticles to thus specifically bind to the target material. The capture-agent/nanoparticle conjugate specifically binds to the target material and absorbs infrared light and emits infrared light, rather than visible light, that is, enables sample permeation because of the long wavelength thereof and generates no background signal, and thus there is no interference between light absorption and light emission, whereby the target material to be detected by the user may be detected with high sensitivity. According to the present invention, the substance to be detected by the user may be quickly diagnosed on site in various kinds of specimens such as saliva, blood, stool, beverages and soil, and the present invention may be applied to a variety of fields, including pathogens such as *Bacillus anthracis* and botulinum neurotoxin, animal viruses such as foot-and-mouth disease and avian influenza, diseases such as cancer and cardiovascular diseases, or biomarkers for pregnancy diagnosis.

The capture-agent/nanoparticle conjugate 100, which absorbs infrared light upon irradiation with infrared light and emits infrared light, is characterized in that the wavelength of infrared light that is absorbed and the wavelength of the infrared light that is emitted are different from each other (for example, infrared light of a long wavelength is absorbed and infrared light of a short wavelength is emitted). Preferably, infrared light having a wavelength of 960 to 980 nm is absorbed and infrared light having a wavelength of 750 to 850 nm is emitted (when infrared light having a wavelength of 750 to 850 nm is emitted, permeability to a biomaterial such as tissue may increase, thus preventing the influence of specimens such as blood, stool, etc.). Furthermore, infrared light exhibits high transmittance even if the specimen is an opaque mixed solution, and may thus be applied to various kinds of specimens such as blood, stool, saliva, beverages, and soil, and it is possible to improve the signal-to-noise ratio without generating autofluorescence. Therefore, the diagnostic kit includes the capture-agent/nanoparticle conjugate described above, thereby solving the problem of low sensitivity of the existing on-site immunoassay diagnostic kit and thus maximizing the sensitivity of the on-site immunoassay diagnostic kit while maintaining the convenience and economic feasibility thereof.

The nanoparticles may be doped with a rare earth element, thereby providing upconverting nanoparticles that absorb long-wavelength light energy and emit short-wavelength light energy through pyrolysis synthesis. Also, the nanoparticles may be further doped with a heterogeneous dopant, whereby the distortion of the crystal structure in the nanoparticles may be increased to some extent, thus enabling very sensitive electron transfer. Accordingly, the nanoparticles may be further increased in emission intensity without any significant change in the size of the nanoparticles.

In an embodiment of the invention, the nanoparticles may include at least one selected from the group consisting of fluorides, oxides, halides, oxysulfides, phosphates, and vanadates. For example, at least one selected from the group consisting of $NaYF_4$, $NaYbF_4$, $NaGdF_4$, $NaLaF_4$, $LaF_3$, $GdF_3$, $GdOF$, $La_2O_3$, $Lu_2O_3$, $Y_2O_3$ and $Y_2O_2S$ may be included. The rare earth element with which the nanoparticles are doped may include a lanthanide element, and the wavelength ranges of light absorbed and emitted by the nanoparticles may be controlled by adjusting the kind and concentration of the rare earth element contained in the nanoparticles. Also, it is possible to provide nanoparticles free of interference of the absorption and emission wavelength ranges of infrared light by adjusting the kind and concentration of the rare earth element. Examples of the rare earth element for attaining the above effects may include at least one selected from the group consisting of Y, Er, Yb, Tm and Nd. More particularly, the rare earth element may include 45 to 55 mol % of Y, 43 to 52 mol % of Yb and 1.5 to 3 mol % of Tm. The emission intensity of the nanoparticles may be controlled by adjusting the kind or concentration of the heterogeneous dopant. Also, examples of the heterogeneous dopant with which the nanoparticles are further doped may include at least one selected from the group consisting of Ca, Si, Ni and Ti.

The nanoparticles doped with the rare earth element and the heterogeneous dopant may be manufactured through a doping process typically known in the art of the present invention, for example, a process disclosed in Qian et al., Small, 5: 2285-2290, 2009; Li et al., Advanced Materials, 20:4765-4769, 2008; Zhao et al., Nanoscale, 5:944-952, 2013; Li et al., Nanotechnology, 19:345606, 2008, which are incorporated herein by reference in their entirety.

The capture agent is configured to specifically bind to the target material contained in the specimen, and may include, for example, an antibody, an aptamer, etc., and binding of the capture agent and the nanoparticles doped with the rare earth element and the heterogeneous dopant includes, but is not limited to, any bond selected from among ionic bonds, covalent bonds, metal bonds, coordination bonds, hydrogen bonds, and van der Waals bonds.

The nanoparticles include a core layer comprising particles doped with a rare earth element, a shell layer surrounding the core layer to thus reduce surface defects so as to improve surface uniformity and further doped with a heterogeneous dopant, and a coating layer formed by coating the outer surface of the shell layer with a monomer or a polymer to thus increase the dispersibility of the nanoparticles in a fluid and facilitate the immobilization of the capture agent, in which the capture agent binds to the coating layer. The nanoparticles have a core-shell structure, thus reducing surface defects to increase surface uniformity, and increasing the extent of monodispersion to maximize infrared light emission efficiency, and the shell layer thereof is additionally doped with the heterogeneous dopant, thereby further increasing the infrared light emission intensity. As for the capture-agent/nanoparticle conjugate, the nanoparticles may be surface-treated with a monomer or a polymer, thereby increasing the dispersibility in a fluid in the specimen, such as water, and facilitating the immobilization of the antibody.

For example, the core layer is provided in the form of nanoparticles in a manner in which 1-octadecene, oleic acid and a rare earth element are mixed to form a homogeneous solution, and the homogeneous solution is mixed with methanol containing sodium hydroxide and ammonium fluoride, stirred, and then allowed to react at a predetermined temperature for a predetermined period of time, and the shell layer is formed at a predetermined thickness on the core layer in a manner in which 1-octadecene, oleic acid, a rare earth element and a heterogeneous dopant are mixed to form a homogeneous solution, and the homogeneous solution is mixed with methanol containing sodium hydroxide and ammonium fluoride and with the core layer, stirred, and then allowed to react at a predetermined temperature for a predetermined period of time.

The polymer for forming the coating layer may include at least one selected from the group consisting of polyacrylic acid (PAA), polyallylamine (PAAM), 2-aminoethyl dihydrogen phosphate (AEP), polyethylene glycol diacid, polyethylene glycol maleimide acid, and polyethylene glycol phosphate ester. The coating layer may be formed through any process typically known in the art, for example, ligand engineering, such as ligand exchange or oleic acid oxidation, ligand attraction, layer-by-layer assembly, surface treatment using silanization, surface polymerization, and the like. Alternatively, surface treatment may be performed using a process disclosed in Photon Upconversion Nanomaterials, Fan Zhang, Springer, 2015, which is incorporated herein by reference in its entirety.

The membrane 3 includes a test line 5, on which a second capture agent reactive to the target material contained in the specimen is immobilized, and a control line 6, on which a third capture agent reactive to the capture agent of the capture-agent/nanoparticle conjugate 100 is immobilized, the test line 5 being located closer to the conjugation pad 2 than the control line 6. The second capture agent may be configured to specifically bind to or react with the target material, and may include an antibody, an aptamer, etc., and the third capture agent may be configured to specifically bind to or react with the capture agent, and may include an antibody, an aptamer, etc.

The target material specifically bound to the capture agent of the capture-agent/nanoparticle conjugate 100 in the conjugation pad 2 moves to the membrane 3, and a portion thereof binds to the second capture agent and is thus immobilized on the test line 5, and a portion thereof may be immobilized on the control line 6 through reaction between the capture agent of the capture-agent/nanoparticle conjugate 100 and the third capture agent.

Since the second capture agent reactive to the target material contained in the specimen is immobilized on the test line 5, whether or not the specimen contains the target material to be analyzed and the concentration thereof may be analyzed through presence or absence of infrared light emission thereof and through emission intensity measurement.

Since the third capture agent reactive to the capture agent of the capture-agent/nanoparticle conjugate 100 is immobilized on the control line 6, whether or not the analysis is effective may be judged by determining whether the specimen has moved to a necessary position through presence or absence of infrared light emission of the control line 6 and whether the capture agent works.

The absorption pad 4 is a pad that absorbs a fluid in the specimen passing through the membrane 3, and the absorption pad 4 may function as a pump that enables the specimen to continuously move from the sample pad 1 to the membrane 3 by absorbing the fluid contained in the specimen moving from the sample pad 1 to the membrane 3. The specimen may be moved from the sample pad 1 to the absorption pad 4 through a specimen-developing solution if necessary, depending on the capacity of the specimen. The specimen-developing solution may be a solution including at least one selected from the group consisting of, for example, PBS (phosphate buffer saline), KCl, NaCl, Tween 20, HEPES (4-(2-hydroxyethyl)-1-piperazineethanesulfonic acid) and $NaN_3$, but is not limited thereto.

The sample pad 1, the conjugation pad 2, the membrane 3, and the absorption pad 4 may include a solid capillary support, and the solid capillary support may be used without limitation, so long as it is a porous polymer capable of functioning as a solid capillary carrier of chemical components such as an antigen, an antibody, an aptamer or a hapten or is a natural, synthetic or synthetically modified natural material having a plurality of pores, and the shape thereof is not limited. For example, the solid capillary support may include at least one selected from the group consisting of cellulosic material, paper, cellulose acetate, nitrocellulose, polyethersulfone, polyethylene, nylon, polyvinylidene fluoride (PVDF), polyester, polypropylene, silica, vinyl chloride, vinyl chloride-propylene copolymer, vinyl chloride-vinyl acetate copolymer, inactivated alumina, diatomaceous earth, $MgSO_4$, cotton, nylon, rayon, silica gel, agarose, dextran, gelatin and polyacrylamide. More particularly, the membrane may include at least one polymer selected from the group consisting of nitrocellulose, polyethersulfone, polyethylene, nylon, polyvinylidene fluoride, polyester and polypropylene. Also, in an embodiment of the invention, the solid capillary support may be provided in the form of a rod, a plate, a tube, a bead, or the like.

The substrate 7 may be used without limitation, so long as it is able to support and transport the sample pad 1, the conjugation pad 2, the membrane 3 and the absorption pad 4, and the substrate may be liquid-impermeable so that the fluid contained in the specimen does not leak through the substrate. The substrate 7 may include, for example, glass, polystyrene, polypropylene, polyester, polybutadiene, polyvinyl chloride, polyamide, polycarbonate, epoxide, methacrylate, polymelamine and the like.

Another embodiment of the present invention pertains to nanoparticles that are doped with a rare earth element and a heterogeneous dopant and also that absorb infrared light and emit infrared light, and still another embodiment of the present invention pertains to a capture-agent/nanoparticle conjugate that specifically binds to a target material and that also absorbs infrared light and emits infrared light, rather than visible light. The nanoparticles are the same as the nanoparticles described above, and the capture-agent/nanoparticle conjugate is the same as the capture-agent/nanoparticle conjugate 100 described above, and thus a detailed description thereof will be omitted.

Figure 2:
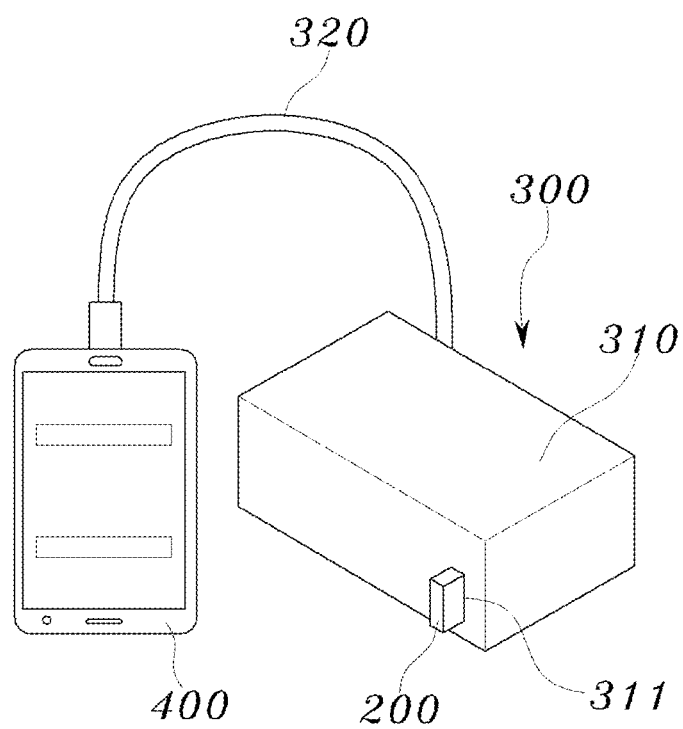
FIG. 2 is a perspective view showing a diagnostic device according to another embodiment of the present invention.
Figure 3:
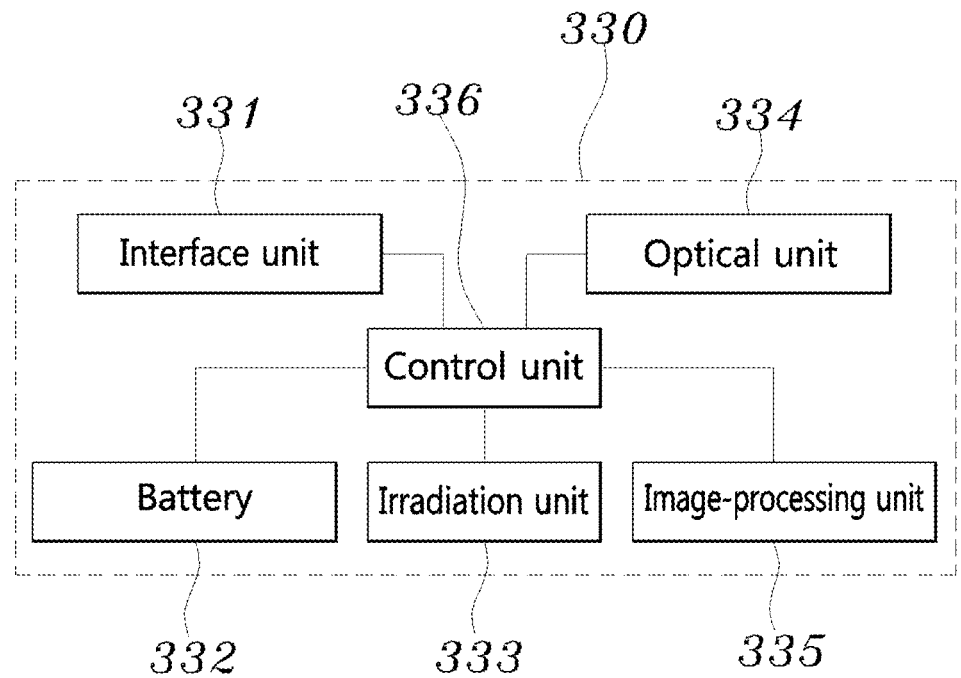
FIG. 3 is a block diagram showing the detailed configuration of the controller of an infrared light reader of FIG. 2.
Figure 4:
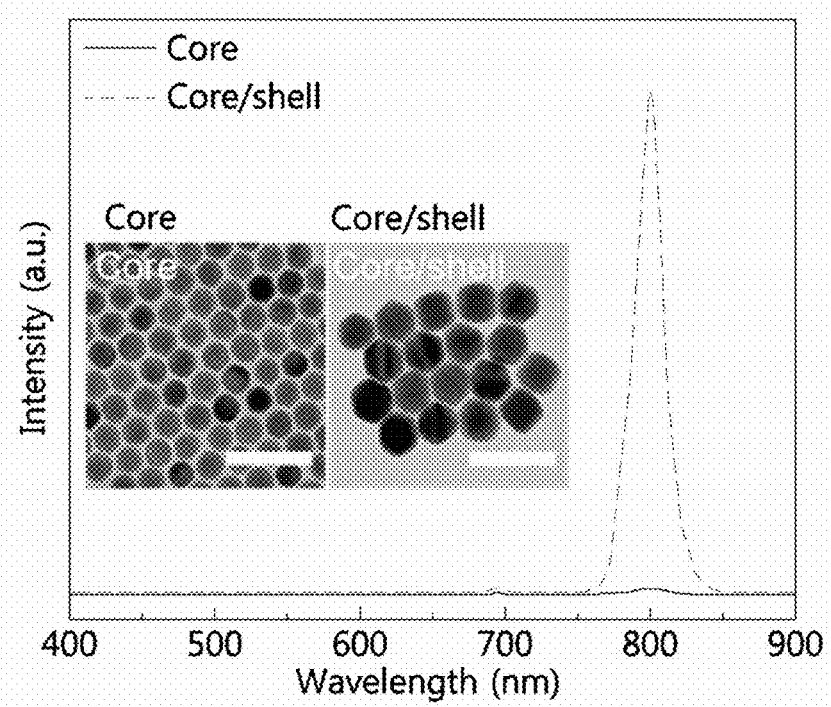
FIG. 4 shows TEM images and an emission spectrum of nanoparticles according to an embodiment of the present invention.

Yet another embodiment of the present invention pertains to a diagnostic device. With reference to FIGS. 1 to 3, the diagnostic device includes the diagnostic kit 200 as described above and an infrared light reader 300.

The infrared light reader 300 is configured to accommodate the diagnostic kit 200 and to apply infrared light to the diagnostic kit 200 and measure infrared light emitted from the diagnostic kit 200 to thus provide imaged data to an external terminal 400, and includes a housing 310, a cable 320, a controller 330, etc.

The housing 310 constitutes the outer shape of the infrared light reader 300, and the housing 310 has an insertion groove 311 into which the diagnostic kit 200 is inserted. The cable 320 connects the controller 330 of the infrared light reader 300 to the terminal 400, and the terminal 400 displays information transmitted from the controller 330, and may include a smartphone, a laptop computer, a tablet computer, or the like.

The controller 330 functions to apply infrared light to the diagnostic kit 200, which is located in the housing 330 and is inserted through the insertion groove 311 in the housing 310, and to measure infrared light emitted from the diagnostic kit 200 so as to provide the imaged data to the external terminal 400, and includes an interface unit 331 for exchanging information with the terminal 400, a battery 332 for supplying power necessary for the operation of the controller 330, an irradiation unit 333 for applying infrared light to the membrane 3 of the diagnostic kit 200 located in the housing 310, an optical unit 334 for photographing infrared light emitted from the membrane 200 after irradiation of the membrane 3 with infrared light by means of the irradiation unit 333, an image-processing unit 335 for digitizing and outputting the photographed image output from the optical unit 334, and a control unit 336 for controlling the overall operation of the controller 330. For example, the irradiation unit 333 plays a role in applying infrared light at a wavelength of 980 nm, and the optical unit 334 includes a visible-light-blocking filter and an ultraviolet-light-blocking filter in order to photograph infrared light. The diagnostic kit 200 where the specimen is dispensed is inserted into the insertion groove 311 in the infrared light reader 300 and the infrared light reader 300 is connected to the terminal 400, whereby the antigen detection result in the diagnostic kit 200 can be confirmed on the terminal 400.

Still yet another embodiment of the present invention pertains to a method of diagnosing a target material using the aforementioned diagnostic device.

The method of diagnosing the target material includes injecting a specimen containing a target material into the sample pad of the diagnostic kit, applying infrared light to the membrane of the diagnostic kit with the infrared light reader after passing the injected specimen through a test line and a control line included in the membrane of the diagnostic kit, and photographing and imaging the infrared light emitted from the membrane irradiated with the infrared light with the infrared light reader.

Particularly, the injecting the specimen containing the target material into the sample pad of the diagnostic kit may include injecting a specimen containing a target material into the sample pad of the diagnostic kit, allowing the target material contained in the specimen to specifically bind to the capture agent of the capture-agent/nanoparticle conjugate in the conjugation pad by moving the specimen to the conjugation pad, immobilizing a portion of the target material on the test line 5 through binding to the second capture agent and a portion of the target material on the control line 6 through reaction of the capture agent of the capture-agent/nanoparticle conjugate 100 and the third capture agent by moving the target material bound to the capture-agent/nanoparticle conjugate to the membrane, and absorbing the target material, which is not immobilized on the test line or the control line of the membrane, to the absorption pad through the membrane.

The injecting the specimen containing the target material into the sample pad of the diagnostic kit may further include adding a specimen-developing solution dropwise on the sample pad of the diagnostic kit after injection of the specimen into the sample pad, thereby facilitating movement of the specimen in the diagnostic kit.

The applying the infrared light to the membrane of the diagnostic kit may be performed in a manner in which infrared light may be applied after the lapse of a predetermined period of time after injection of the specimen containing the target material into the sample pad of the diagnostic kit. Here, the predetermined period of time indicates the time required to pass the specimen containing the target material through the test line and the control line included in the membrane of the diagnostic kit, and is not limited, but may fall in the range of, for example, about 5 min to 30 min, and particularly about 5 min to 20 min.

A better understanding of the present invention will be given through the following examples, which are set forth to illustrate but are not to be construed as limiting the scope of the present invention.

<Example 1> Preparation of Nanoparticles Absorbing and Emitting Infrared Light (1) Formation of Core 1-octadecene, oleic acid, yttrium acetate hydrate, ytterbium acetate hydrate and thulium acetate hydrate were mixed (particularly, 7 mL of 1-octadecene and 3 mL of oleic acid were mixed with 0.4 mmol of lanthanide (comprising 50 mol % of Y, 48 mol % of Yb and 2 mol % of Tm)), and were then heated at 150° C. to afford a homogeneous solution, which was then cooled to 50° C. 5 mL of methanol containing 1 mmol NaOH and 1.6 mmol $NH_4F$ was added to the homogeneous solution and stirred for 30 min, thus forming a mixed solution. In order to remove methanol, the mixed solution was maintained at 100° C. for 10 min, and was then maintained in an argon gas atmosphere at 290° C. for 1 hr 30 min. After natural cooling of the mixed solution, the nanoparticles were precipitated in ethanol and washed three times with cyclohexane and ethanol, thus obtaining nanoparticles (core).

(2) Formation of Shell (Formation of UCNPs)

1-octadecene, oleic acid, yttrium acetate hydrate and calcium acetate hydrate were mixed (particularly, 7 mL of 1-octadecene and 3 mL of oleic acid were mixed with 0.2 mmol of a dopant (comprising 85 mol % of lanthanide (Y) and 15 mol % of a heterogeneous dopant (Ca))), and were then heated at 150° C. to afford a homogeneous solution, which was then cooled to 50° C. 5 mL of methanol containing 1 mmol NaOH and 1.6 mmol $NH_4F$, the homogeneous solution and the nanoparticles (core) prepared in (1) of Example 1 were mixed and stirred for 30 min, thus forming a mixed solution. In order to remove methanol, the mixed solution was maintained at 100° C. for 10 min, and was then maintained in an argon gas atmosphere at 290° C. for 1 hr 30 min. After natural cooling of the mixed solution, the nanoparticles were precipitated in ethanol and washed three times with cyclohexane and ethanol, thus obtaining nanoparticles (core/shell, UCNPs) having a core-shell structure.

<Example 2> Preparation of Capture Agent (Antibody)-Nanoparticle Conjugate (1) Formation of Coating Layer The nanoparticles (core/shell) were coated with a polymer using a ligand engineering process. The nanoparticles prepared in (2) of Example 1 were dispersed in 13.4 mL of tetrahydrofuran to give a nanoparticle solution, and 100 mg of dopamine hydrochloride dispersed in 600 µL of distilled water was added to the nanoparticle solution, thus forming a solution mixed with nanoparticles, which was then maintained in an argon gas atmosphere at 50° C. for 5 hr. After natural cooling of the solution mixed with nanoparticles, addition with 16 µL of hydrochloric acid and then washing two times with distilled water were performed, thus obtaining amine-group-containing nanoparticles ($NH_2$—UCNPs).

(2) Antibody Binding (Formation of Antibody-Nanoparticle Conjugate)

1 µL of a solution formed by mixing 2.1 mg of SATA (N-succinimidyl-S-acetyl-thioacetate), 61 µL of dimethyl sulfoxide and 182 µL of 10 mM HEPES (4-(2-hydroxyethyl)-1-piperazineethanesulfonic acid) was added with 25 µg of an anti-nucleoprotein antibody (anti-human CRP antibody, first antibody) capturing the nucleoprotein of avian influenza virus (H5N6), allowed to react at room temperature for 30 min, further added with 12.5 µL of a 0.5 M hydroxylamine hydrochloride solution, and allowed to react for 2 hr, after which the reaction residue was removed using a 100 k filter tube, thereby obtaining a thiolated antibody. 1.875 mg of the amine-group-containing nanoparticles prepared in (1) of Example 2, 1 mL of distilled water and 12.5 μL of 1 M HEPES buffer solution were mixed to give a first solution, and 18.8 mg of sulfo-SMCC (sulfosuccinimidyl 4-(N-maleimidomethyl)cyclohexane-1-carboxylate) was added to 100 μL of a 10 mM HEPES buffer solution to give a second solution. The first solution was mixed with 1 μL of the second solution and allowed to react for 2 hr, after which the reaction residue was removed using a 100 k filter tube, thus obtaining maleimidated nanoparticles. The thiolated antibody and the maleimidated nanoparticles were added to a HEPES buffer solution, allowed to react at 4° C. for 24 hr and then centrifuged, thus obtaining antibody-immobilized nanoparticles (antibody-nanoparticle conjugate).

<Example 3> Manufacture of Diagnostic Kit Using Antibody-Nanoparticle Conjugate (1) A sample pad was thoroughly wetted with a 10 mM HEPES buffer solution containing 0.3% (w/v) PVP (polyvinylpyrrolidone), completely dried, and then cut to a size of 4 mm×20 mm. An absorption pad was dehydrated before use. A nitrocellulose membrane was laminated on a plastic card (a substrate) using a laminator, after which the second antibody (anti-nucleoprotein having an epitope different from that of the first antibody), reactive to the antigen contained in the specimen, was dispensed on the test line T and the third antibody (anti-goat antibody) reactive to the first antibody immobilized on the antibody-nanoparticle conjugate was dispensed on the control line C using an automatic dispenser, followed by drying at room temperature for 48 hr. A conjugation pad was thoroughly wetted with a 10 mM HEPES buffer solution containing 2.0% (w/v) BSA (Bovine Serum Albumin), 2.0% (w/v) Tween 20, 2.5% (w/v) sucrose and 0.3% (w/v) PVP, followed by drying in an oven, dispensing of the antibody-nanoparticle conjugate solution prepared in Example 2 thereon, and complete drying in an oven before use.

(2) As shown in FIG. 1, the sample pad, the conjugation pad, the membrane located on the substrate and the absorption pad were disposed in an overlapping manner, fixed, and placed in a plastic box, thus manufacturing a diagnostic kit.

<Test Example 1> Evaluation of Size, Shape and Emission Spectrum of Nanoparticles (1) The nanoparticles (core) prepared in (1) of Example 1 and the nanoparticles (core/shell) prepared in (2) of Example 1 were evaluated with a Talos F200X TEM having an acceleration voltage of 200 kV, and the emission spectra of respective nanoparticle-dispersed solutions were measured using an NIR spectrometer through irradiation with infrared light at 980 nm. The results are shown in FIG. 4.

(2) As shown in FIG. 4, the nanoparticles (core, core/shell) were spherical overall in shape and had a diameter of tens of nm, and the core and the core/shell had different emission intensities. This is because the formation of the shell on the core reduces the incidence of surface defects, thus increasing surface uniformity and enhancing light emission by the heterogeneous dopant.

<Test Example 2> Evaluation of Size, Shape and Emission Spectrum of Nanoparticles Depending on the Amount of Heterogeneous Dopant (1) UCNPs were prepared in the same manner as in Example 1, with the exception that the total mol number of the dopant in Example 1 was maintained and that the ratio of lanthanide (Y) and heterogeneous dopant (Ca) was adjusted. In FIGS. 5 to 8, 0% Ca designates the dopant comprising 100 mol % of lanthanide (Y), 5% Ca designates the dopant comprising 95 mol % of lanthanide (Y) and 5 mol % of the heterogeneous dopant (Ca), 10% Ca designates the dopant comprising 90 mol % of lanthanide (Y) and 10 mol % of the heterogeneous dopant (Ca), 15% Ca designates the dopant comprising 85 mol % of lanthanide (Y) and 15 mol % of the heterogeneous dopant (Ca), and 20% Ca designates the dopant comprising 80 mol % of lanthanide (Y) and 20 mol % of the heterogeneous dopant (Ca).

Figure 5:
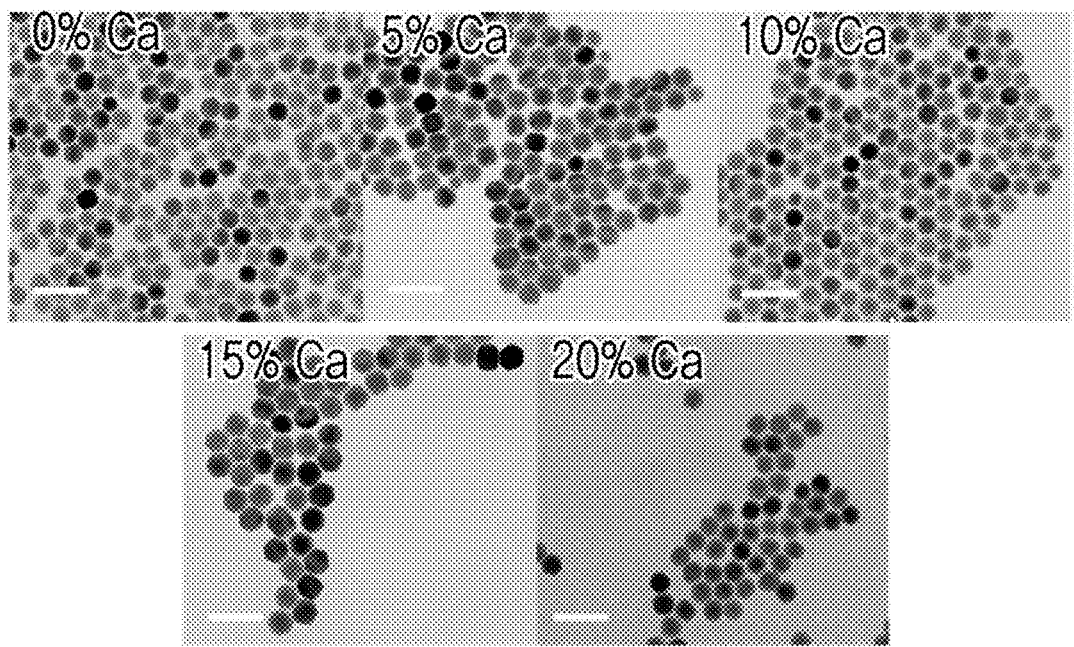
FIG. 5 shows TEM images of nanoparticles manufactured using a heterogeneous dopant in different amounts.
Figure 6:
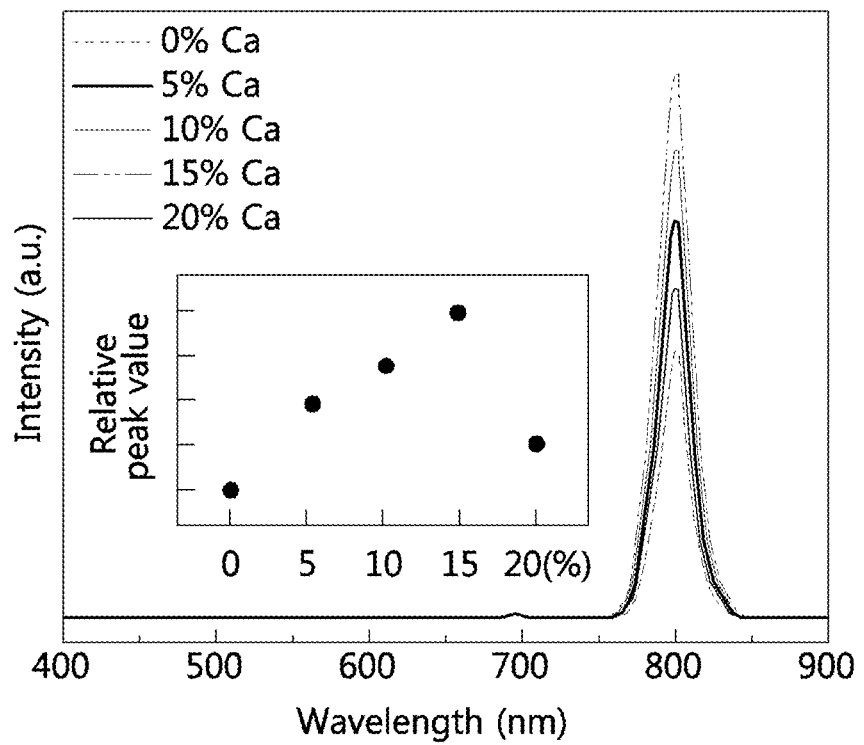
FIG. 6 shows the results of emission spectra of nanoparticles manufactured using a heterogeneous dopant in different amounts.

(2) The UCNPs prepared in (2) of Example 1 and the UCNPs prepared in (1) of Test Example 2 were evaluated with a Talos F200X TEM having an acceleration voltage of 200 kV. The results are shown in FIG. 5. The emission spectra of respective nanoparticle-dispersed solutions were measured using an NIR spectrometer through irradiation with infrared light at 980 nm. The results are shown in FIG. 6.

(3) As shown in FIG. 5, the UNCPs were spherical overall in shape and had a diameter of tens of nm, indicating that the diameter thereof was not greatly changed even by the addition of the heterogeneous dopant. Furthermore, as seen in FIG. 6, it can be found that the concentration of the heterogeneous dopant that was added had an influence on the emission intensity.

Figure 7:
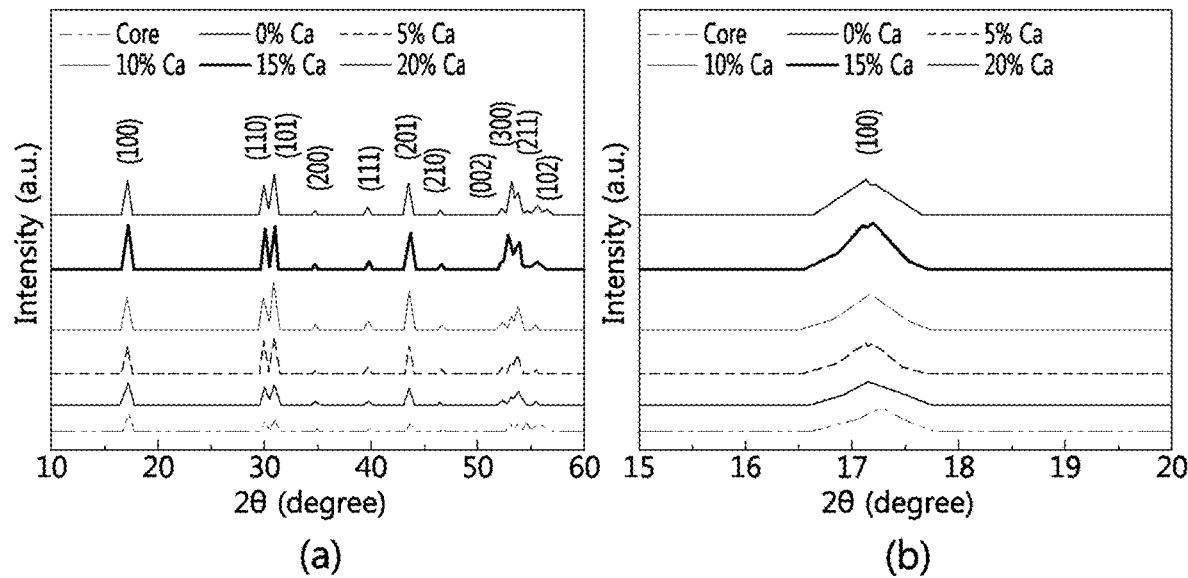
FIG. 7 shows the results of analysis of the crystal structure of nanoparticles manufactured using a heterogeneous dopant in different amounts.
Figure 8:
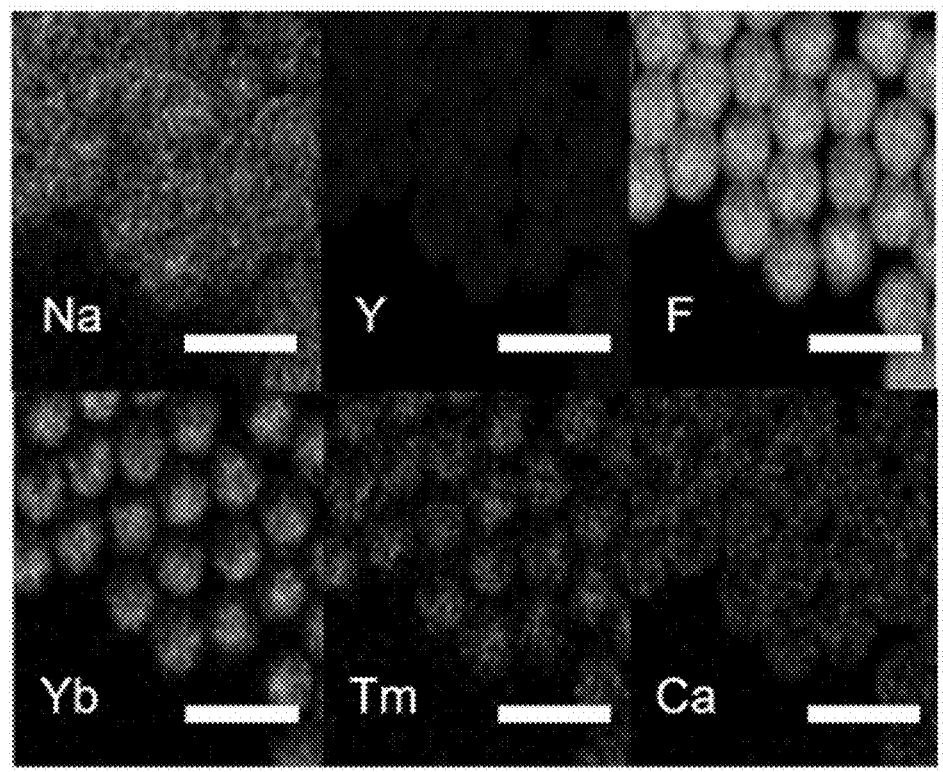
FIG. 8 shows the results of elemental analysis of nanoparticles according to an embodiment of the present invention.

<Test Example 3> Analysis of Crystal Structure of Nanoparticles and Elemental Analysis Thereof (1) Each of the solutions in which the nanoparticles prepared in (1) of Example 1, (2) of Example 1 and (1) of Test Example 2 were dispersed was dispensed on a silicon wafer, and the crystal structure of the nanoparticles was analyzed using an XRD-7000. The results are shown in FIG. 7. The elemental analysis of the nanoparticles prepared in (2) of Example 1 was performed using a Talos F200X TEM having an acceleration voltage of 200 kV. The results are shown in FIG. 8. Particularly, elemental analysis was conducted through energy dispersive X-ray spectroscopy mapping in the state in which the photography mode was changed to obtain a dark field image in TEM.

(2) As shown in FIG. 7($a$), the crystal structures of UCNPs having core, and lanthanide (Y) and heterogeneous dopant (Ca) at different ratios were similar to some extent, and as shown in FIG. 7($b$), in which the 15° to 20° portion of 2 theta is enlarged in the image of FIG. 7($a$), the peak value was shifted gradually to the left in the (100) crystal orientation. Thus, it can be found that the concentration of the heterogeneous dopant that is added has some influence on the crystal structure.

(3) As shown in FIG. 8, Na, Y, and F were distributed throughout the nanoparticles, and Yb and Tm were distributed in the core layer and Ca was distributed in the shell layer, indicating that UCNPs in which the shell layer includes the heterogeneous dopant were efficiently synthesized.

Figure 9:
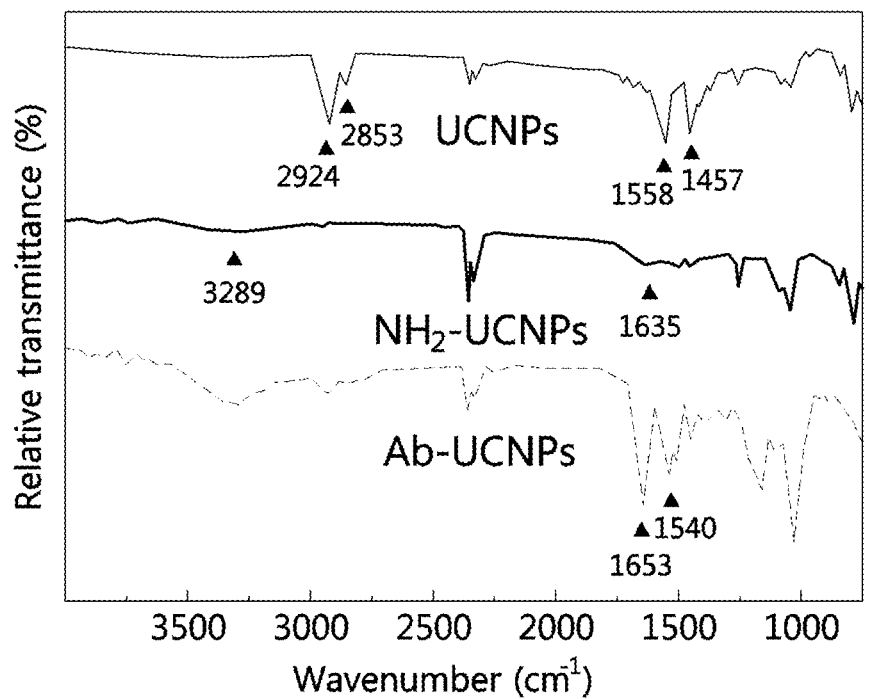
FIG. 9 shows the results of infrared spectroscopy of nanoparticles according to an embodiment of the present invention.

<Test Example 4> Evaluation of Antibody Binding to Nanoparticles (1) The UCNPs prepared in (2) of Example 1, the $NH_2$—UCNPs prepared in (1) of Example 2 and the antibody-immobilized nanoparticles (Ab-UCNPs) prepared in (2) of Example 2 were subjected to Fourier transform infrared spectroscopy using an iS10 Fourier transform infrared spectrophotometer. The results are shown in FIG. 9. Also, the $NH_2$—UCNPs and the antibody-nanoparticle conjugate (Ab-UCNPs) prepared in (2) of Example 2 were measured for surface charge (zeta potential) using a Zetasizer (Zetasizer Nano ZS90, Malvern). The results are shown in FIG. 10.

(2) As shown in FIG. 9, UNCPs had peaks at 1457 and 1558 $cm^{-1}$ corresponding to the asymmetric and symmetric vibrations of the COO— group, respectively, and transmission bands at 2853 and 2924 $cm^{-1}$, corresponding to the asymmetric and symmetric vibrations of —$CH_2$ in the alkyl chain of the oleic acid. $NH_2$—UCNPs had bands at 1635 and 3289 $cm^{-1}$ corresponding to the C—N and N—H vibrations of the amine group, respectively, and Ab-UCNPs had peaks at 1540 and 1653 $cm^{-1}$ corresponding to the amide bond, from which the antibody was confirmed to bind to the nanoparticles.

Figure 10:
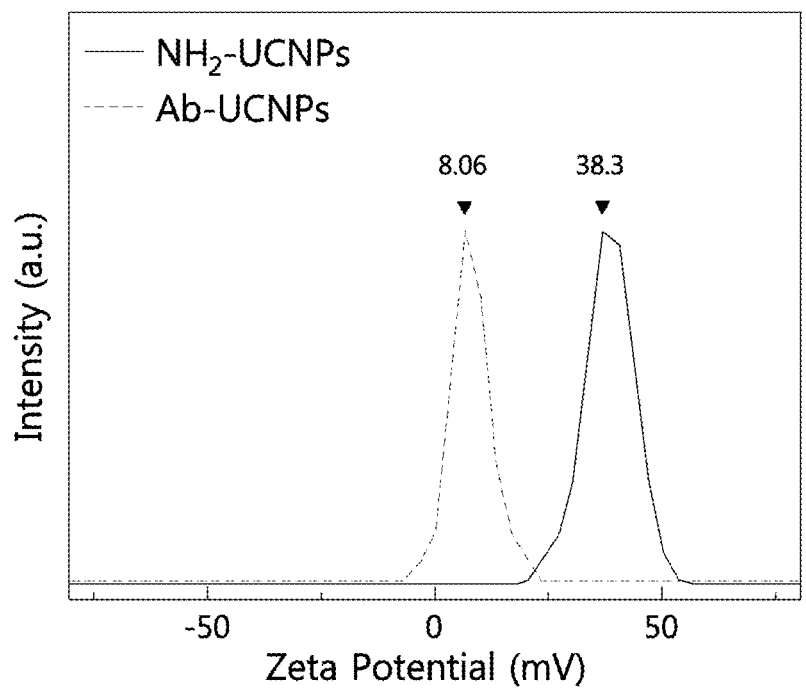
FIG. 10 shows the results of measurement of surface charge of a capture-agent/nanoparticle conjugate according to an embodiment of the present invention.

(3) As shown in FIG. 10, the zeta potential of $NH_2$-UCNPs and Ab-UCNPs changed from 38.3 mV to 8.06 mV, and immobilization of the antibody on the nanoparticles was confirmed.

Figure 11:
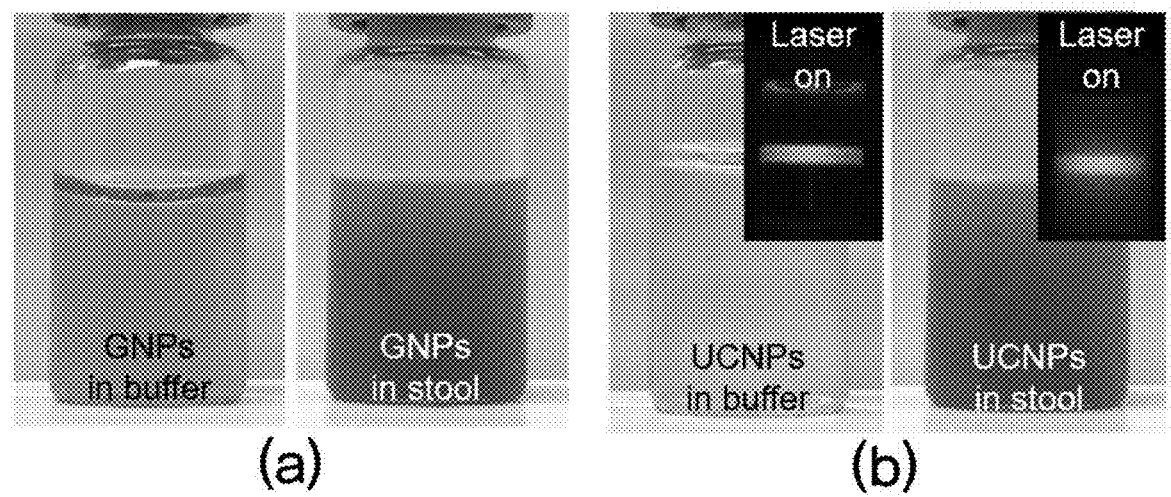
FIG. 11 shows camera images for evaluating infrared light emission capability of nanoparticles according to an embodiment of the present invention.
Figure 12:
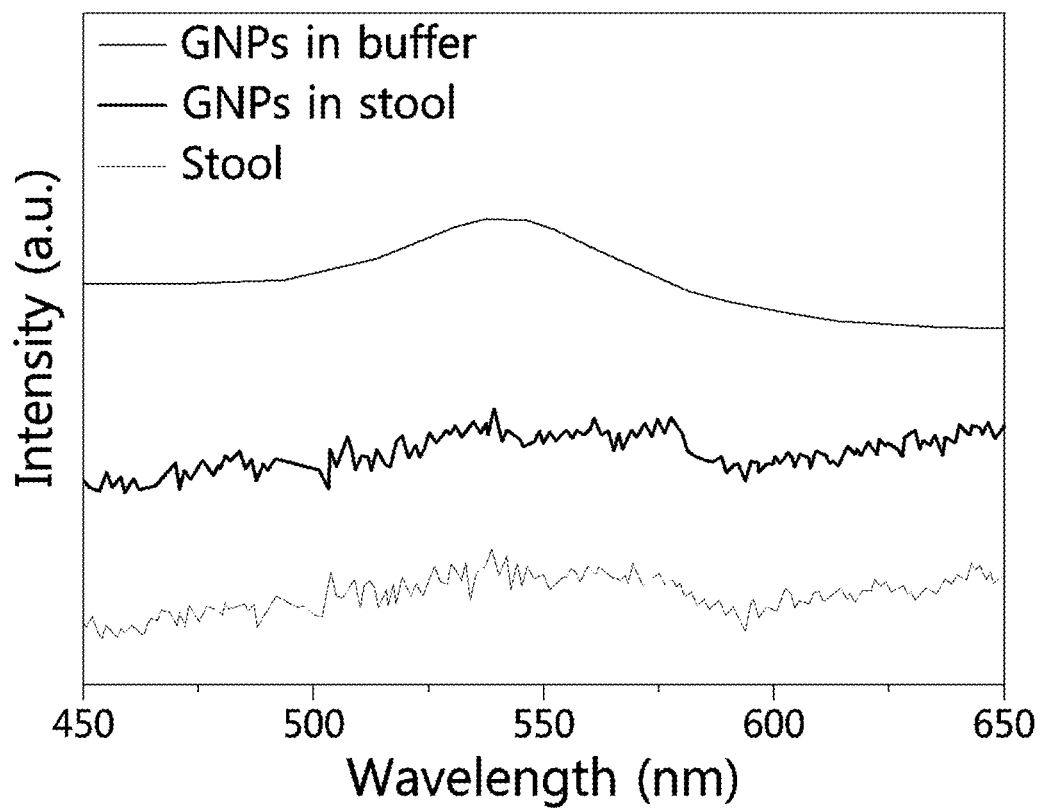
FIG. 12 shows the results of absorption spectra of conventional gold nanoparticles.
Figures 13, 14:
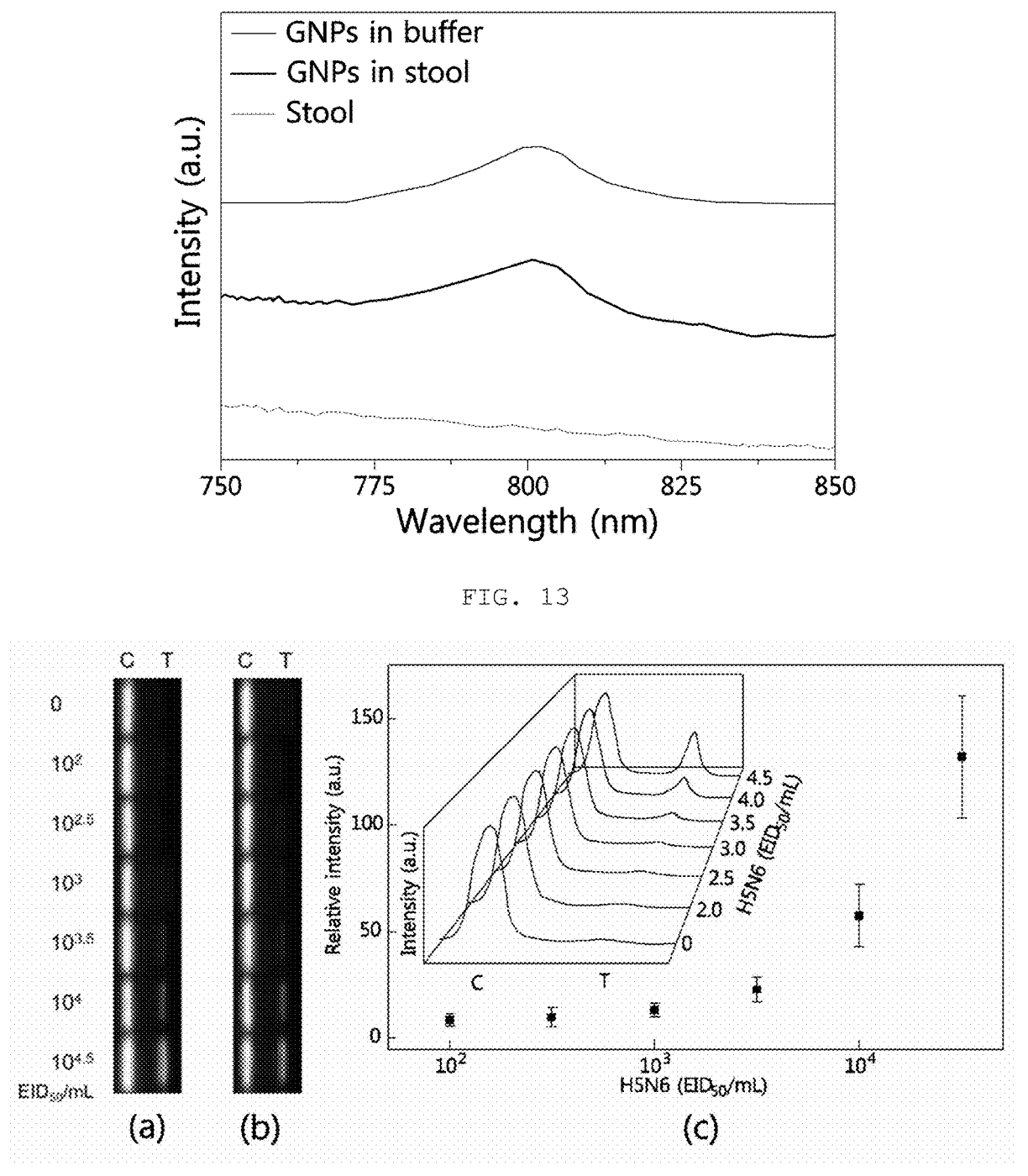

<Test Example 5> Evaluation of Infrared Light Emission Capability of Nanoparticles (1) Gold nanoparticles (GNPs) were dispersed in a buffer solution and a duck-stool-containing buffer solution and photographed using a normal camera. The results are shown in FIG. 11($a$). The nanoparticles (UCNPs) prepared in (2) of Example 1 were dispersed in a buffer solution and a duck-stool-containing buffer solution, photographed using a normal camera, irradiated with infrared light at a wavelength of 980 nm, and photographed using an infrared light camera for photographing an infrared light image at 800 nm. The results are shown in FIG. 11($b$). Moreover, the duck-stool-containing buffer solution (stool), the gold-nanoparticle-dispersed buffer solution (GNPs in buffer) and the gold-nanoparticle-dispersed duck-stool-containing buffer solution (GNPs in stool) were measured for absorption spectra using a UV/VIS/NIR spectrometer. The results are shown in FIG. 12. Also, the duck-stool-containing buffer solution (stool), the UCNP-dispersed buffer solution (UCNPs in buffer) and the UCNP-dispersed duck-stool-containing buffer solution (UCNPs in stool) were irradiated with infrared light at a wavelength of 980 nm and measured for emission spectra using a NIR spectrometer. The results are shown in FIG. 13. The gold nanoparticles were obtained by adding 20 mL of a 1 mM $HAuCl_4$ solution with 2 mL of a 1% trisodium citrate dihydrate solution, followed by reaction for 10 min and centrifugation.

(2) As shown in FIG. 11($a$), when the gold nanoparticles were dispersed in the buffer solution (buffer), a red color was observed, but a red color was not observed when the gold nanoparticles were dispersed in the opaque stool-containing buffer solution (stool). As shown in FIG. 11($b$), when the nanoparticles prepared in (2) of Example 1 were irradiated with infrared light at a wavelength of 980 nm, infrared light at a wavelength of about 800 nm was emitted upon dispersion both in the buffer solution (buffer) and in the stool-containing buffer solution (stool) (represented by 'Laser on' in the drawings).

(3) As shown in FIG. 12, when the gold nanoparticles were dispersed in the opaque stool-containing buffer solution, an absorption peak at a wavelength of 550 nm was not observed, but as shown in FIG. 13, infrared light at a wavelength of 800 nm was emitted in both the UCNP-dispersed buffer solution and the UCNP-dispersed opaque stool-containing buffer solution.

<Test Example 6> Analysis of Specimen Using Diagnostic Kit (1) A specimen-developing solution (comprising a H5N6 antigen and a transparent buffer solution) having different concentrations of nucleoprotein (C-reactive protein (CRP)) of avian influenza virus (H5N6) was added dropwise on the sample pad of the diagnostic kit of Example 3. After 20 min, infrared light at a wavelength of 980 nm was applied thereto, and photography with an infrared light camera was performed. The results are shown in FIG. 14(a).

(2) The test was performed in the same manner as in (1) of Test Example 5, with the exception that the stool-containing buffer solution was used in lieu of the transparent buffer solution. The results are shown in FIG. 14(b), and the emission intensities of two lines C, T are shown in FIG. 14(c).

(3) As shown in FIG. 14, the viral detection limit was $10^{3.5}$ $EID_{50}$/mL, and the emission intensity of the test line was increased with an increase in the viral concentration, from which the target material of interest can be confirmed to be easily detected using the diagnostic kit. Moreover, regardless of whether the transparent buffer solution or the stool-containing buffer solution (opaque) was used in the specimen-developing solution, it was not difficult to confirm the viral detection results on the test line, from which the virus can be concluded to be stably detected on site using the above diagnostic kit.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. Nanoparticles that are used on-site immunoassay diagnostic kits and move with the specimen and absorb infrared light and emit infrared light, doped with a rare earth element and a heterogeneous dopant and absorbing infrared light and emitting infrared light,
    wherein the nanoparticles comprises a core layer doped with a rare earth element and a shell layer surrounds the core layer for increasing a uniformity of the core layer by reducing surface defects and further doped with a heterogeneous dopant,
    wherein the core layer is provided in a form of nanoparticles by heating a solution containing the rare earth element to form a homogeneous solution, and mixing a mixed solution containing a sodium compound and a fluorine compound with the cooled homogeneous solution, and reacting by applying heat,
    wherein the shell layer is formed on the core layer to a predetermined thickness by mixing the nanoparticle form of the core layer and the heterogeneous dopants in the mixed solution and then reacting by applying heat,
    wherein the core layer is in a form of a hexagonal and the nano particles have a round shape morphology,
    wherein the rare earth element includes 50 mol % of Y, 48 mol % of Yb and 2 mol % of Tm.

2. The nanoparticles of claim 1, wherein emission intensity of the nanoparticles is controlled by adjusting a kind or concentration of the heterogeneous dopant.

3. Nanoparticles that are used on-site immunoassay diagnostic kits and move with the specimen and absorb infrared light and emit infrared light, doped with a rare earth element and a heterogeneous dopant and absorbing infrared light and emitting infrared light,
    wherein the nanoparticles comprises a core layer doped with a rare earth element and a shell layer surrounds the core layer for increasing a uniformity of the core layer by reducing surface defects and further doped with a heterogeneous dopant,
    wherein the core layer is provided in a form of nanoparticles by heating a solution containing the rare earth element to form a homogeneous solution, and mixing a mixed solution containing a sodium compound and a fluorine compound with the cooled homogeneous solution, and reacting by applying heat,
    wherein the shell layer is formed on the core layer to a redetermined thickness by mixing the nanoparticle form of the core layer and the heterogeneous dopants in the mixed solution and then reacting by applying heat,
    wherein the core layer is in a form of a hexagonal and the nano particles have a round shape morphology,
    wherein the heterogeneous dopant includes at least one selected from the group consisting of Ca, Si, Ni and Ti.

4. The nanoparticles of claim 1, wherein the nanoparticles are configured such that a wavelength of infrared light that is absorbed and a wavelength of infrared light that is emitted are different from each other so that there is no interference between infrared light that is absorbed and infrared light that is emitted.

5. The nanoparticles of claim 1, wherein the nanoparticles absorb infrared light having a wavelength of 960 to 980 nm and emit infrared light having a wavelength of 750 to 850 nm.

6. The nanoparticles of claim 1, wherein the nanoparticles further include a coating layer formed on an outer surface of the shell layer through coating with a monomer or a polymer to increase dispersibility of the nanoparticles in a fluid and facilitate immobilization of a capture agent.

7. The nanoparticles of claim 3, wherein emission intensity of the nanoparticles is controlled by adjusting a kind or concentration of the heterogeneous dopant.

8. The nanoparticles of claim 3, wherein the rare earth element includes at least one selected from the group consisting of Y, Er, Yb, Tm and Nd.

9. The nanoparticles of claim 3, wherein the nanoparticles are configured such that a wavelength of infrared light that is absorbed and a wavelength of infrared light that is emitted are different from each other so that there is no interference between infrared light that is absorbed and infrared light that is emitted.

10. The nanoparticles of claim 3, wherein the nanoparticles absorb infrared light having a wavelength of 960 to 980 nm and emit infrared light having a wavelength of 750 to 850 nm.

11. The nanoparticles of claim 3, wherein the nanoparticles further include a coating layer formed on an outer surface of the shell layer through coating with a monomer or a polymer to increase dispersibility of the nanoparticles in a fluid and facilitate immobilization of a capture agent.

\* \* \* \* \*